US00PP19813P2

(12) United States Plant Patent
Verschoor

(10) Patent No.: US PP19,813 P2
(45) Date of Patent: Mar. 10, 2009

(54) ***PHLOX* PLANT NAMED 'SWIZZLE'**

(50) Latin Name: *Phlox paniculata hybid*
Varietal Denomination: Swizzle

(75) Inventor: Jan Verschoor, Haarlem (NL)

(73) Assignee: Witteman & Co, Hillegom (NL)

( * ) Notice: Subject to any disclaimer, the term of this patent is extended or adjusted under 35 U.S.C. 154(b) by 0 days.

(21) Appl. No.: 11/998,265

(22) Filed: Nov. 29, 2007

(51) Int. Cl.
*A01H 5/00* (2006.01)

(52) U.S. Cl. ..... Plt./320
(58) Field of Classification Search ..... Plt./320
See application file for complete search history.

*Primary Examiner*—Annette H Para
*Assistant Examiner*—Georgia Helmer
(74) *Attorney, Agent, or Firm*—Jondle & Associates, P.C.

(57) ABSTRACT

A new *phlox* plant particularly distinguished by pinkish-white overlapping petals around an intense, hot-pink eye, compact plant habit, healthy foliage and good mildew resistance is disclosed.

2 Drawing Sheets

Genus and species: *Phlox paniculata hybid.*
Variety denomination: 'Swizzle'.

BACKGROUND OF THE NEW PLANT

The present invention comprises a new and distinct cultivar of *phlox,* botanically known as *Phlox paniculata,* and hereinafter referred to by the cultivar name 'Swizzle'. The new cultivar originated from an open pollination in 2005 in a cultivated field in Haarlem, The Netherlands between unknown male and female *Phlox paniculata* plants.

The new cultivar was selected from the results of the open pollination in 2006 in Haarlem, The Netherlands on the basis of healthy foliage, unique flower color and better mildew resistance and has been asexually reproduced through two generations by vegetative cuttings in Haarlem, The Netherlands since that time. The present invention has been found to retain its distinctive characteristics through successive asexual propagations.

SUMMARY OF THE INVENTION

The following are the most outstanding and distinguishing characteristics of this new cultivar when grown under normal horticultural practices in Haarlem, The Netherlands.

1. Pinkish-white overlapping petals around an intense, hot-pink eye;
2. Compact habit;
3. Healthy foliage; and
4. Good mildew resistance.

DESCRIPTION OF PHOTOGRAPHS

This new *phlox* plant is illustrated by the accompanying photographs which show blooms and foliage of the plant in full color, the colors shown being as true as can be reasonably obtained by conventional photographic procedures. The photographs are of a 2-year-old plant grown outdoors in Haarlem, The Netherlands.

DESCRIPTION OF THE NEW CULTIVAR

Figure 1:
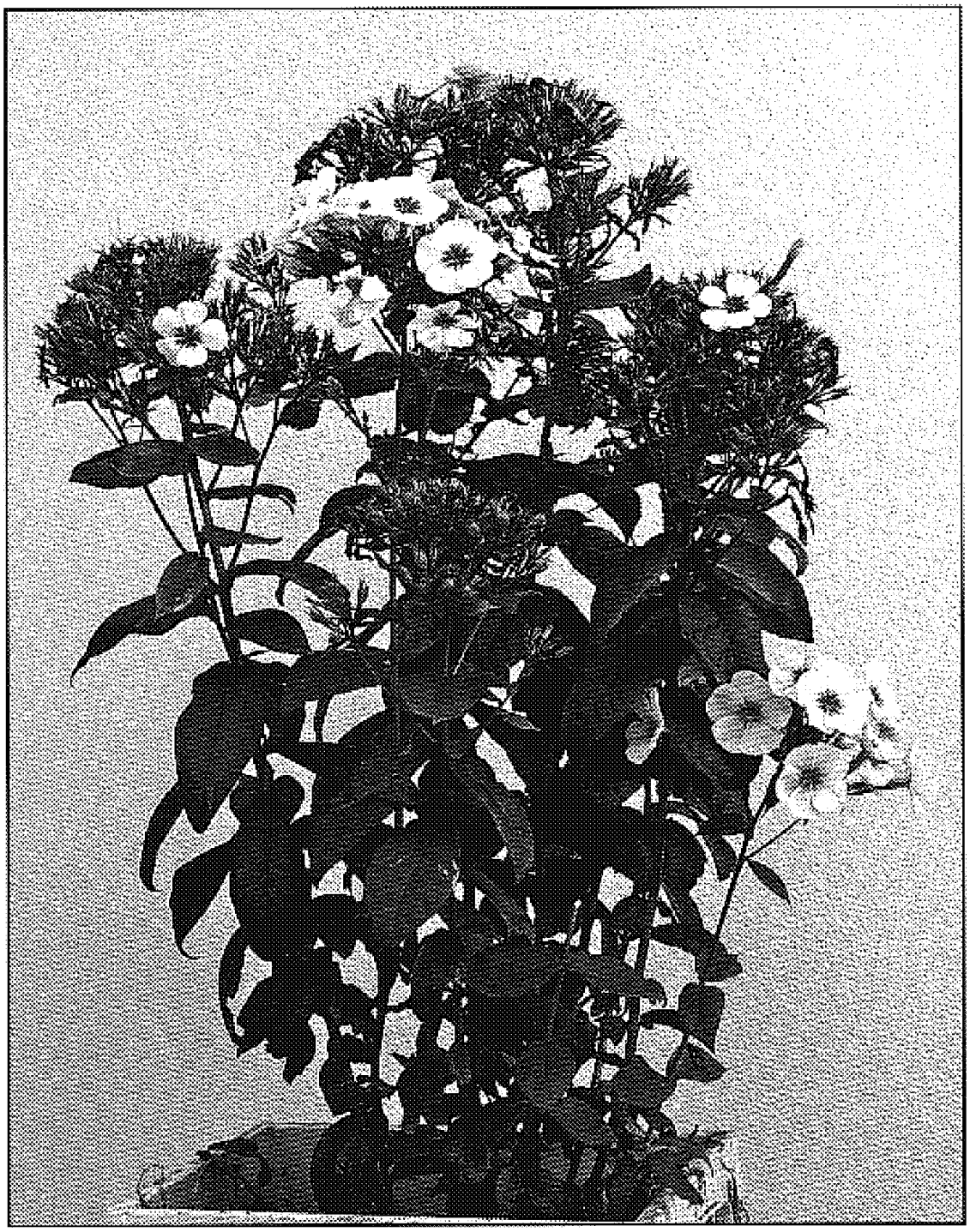
FIG. 1 shows the overall plant habit, including blooms, buds and foliage.
Figure 2:
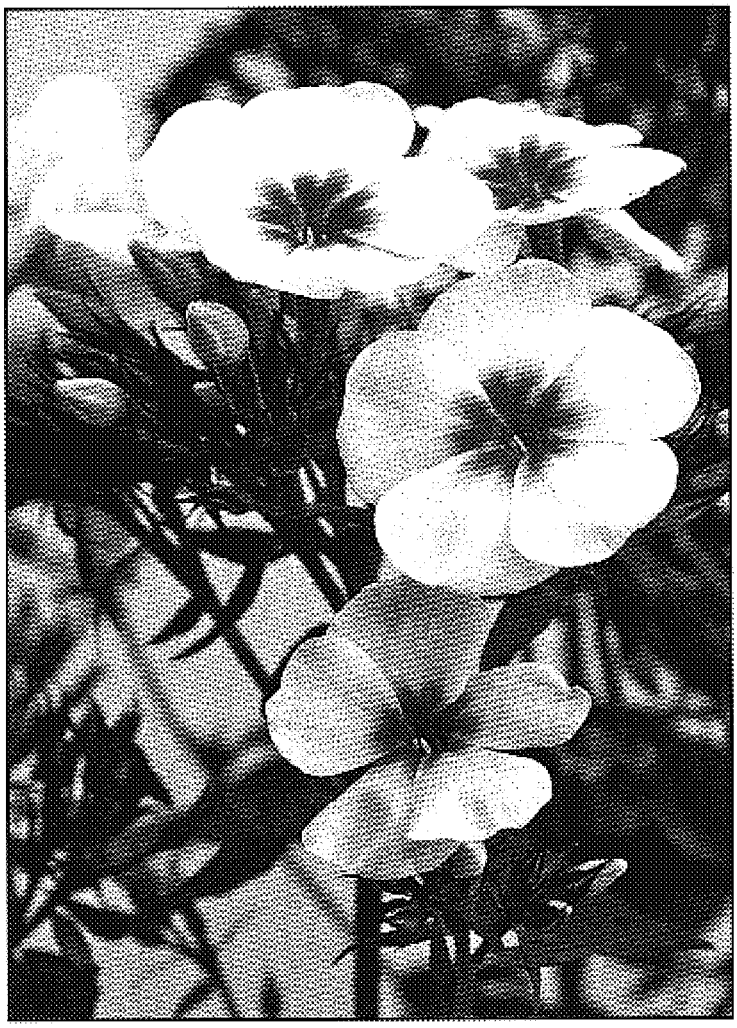
FIG. 2 shows flower buds and mature flowers.
Figure 3:
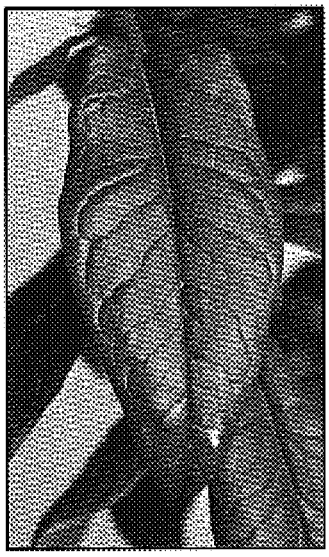
FIG. 3 shows a mature leaf of the plant.

The following detailed description sets forth the distinctive characteristics of 'Swizzle'. The data which define these characteristics were collected from asexual reproductions carried out in Haarlem, The Netherlands. The plant history was taken in August on 2 year old plants which were planted and grown outdoors in daytime temperatures between 14° C. and 32° C. and nighttime temperatures between 5° C. and 15° C. No pinchings, growth retardants or photoperiodic treatments were used. Observations were made when the plants were in natural outdoor light. Color references are primarily to the R.H.S. Colour Chart of The Royal Horticultural Society of London (R.H.S.) (2001).

DETAILED BOTANICAL DESCRIPTION

Classification:
- *Family.*—Polemoniaceae.
- *Botanical.*—*Phlox paniculata.*
- *Common name.*—*Phlox.*

Parentage:
- *Female parent.*—Unknown individual plant of *Phlox paniculata.*
- *Male parent.*—Unknown individual plant of *Phlox paniculata.*

Growth:
- *Form.*—Herbaceous perennial.
- *Habit.*—Upright, moderate vigor.
- *Shape.*—Narrow inverted triangle.
- *Height (measured from the top of the soil).*—53.3 cm.
- *Diameter.*—37.4 cm.
- *Growth rate.*—13.0 cm per month.
- *Flowering response.*—9 months.
- *Time to produce a finished flowering plant.*—25 weeks from rooted cutting for a 1.5 liter container.
- *Time to initiate and develop roots during summer.*—30 days.
- *High temperature tolerance.*—Tolerant to at least 35° C.
- *Lower temperature tolerance.*—Hardy to USDA Zone 4.
- *Roots.*—White, thin, fibrous, sparse, freely branching.

Branches:
*Habit.*—Moderate basal branching.
*Number of branches.*—8 flowering stems.
Stems:
*Description.*—Round, glaborous, slightly glossy.
*Aspect.*—Rounded.
*Color.*—RHS 144A (Yellow-green).
*Diameter.*—0.4 cm.
*Stem length* (*excluding inflorescence*).—30.9 cm.
*Internode length.*—2.8 cm.
*Strength.*—Strong.
*Pubescence.*—Absent.
Leaves:
*Arrangement.*—Opposite, single.
*Quantity of leaves* (*per lateral branch*).—22.
*Durability to stress.*—High.
*Shape.*—Broadly elliptic to ovate.
*Apex.*—Apiculate.
*Base.*—Truncate.
*Color* (*mature leaves*).—Upper surface: Between RHS 139A (Green) and RHS 147A (Yellow-green). Lower surface: Between RHS 137A (Green) and RHS 137B (Green).
*Color* (*immature leaves*).—Upper surface: RHS 141A (Green). Lower surface: RHS 138A (Green).
*Margin.*—Revolute, very short, fine serration (approx. 30 teeth per cm).
*Size.*—Length: 8.6 cm. Width: 3.9 cm.
*Texture* (*upper surface*).—Smooth, glabrous.
*Pubescence.*—Absent.
*Venation.*—Type: Pinnate. Color: Upper surface: RHS 145A (Yellow-green). Lower surface: RHS 144B (Yellow-green).
*Petiole.*—Shape: V-shaped. Length: 0.3 cm. Diameter: 0.35 cm. Color (Both surfaces): RHS 144B (Yellow-green).
Flower buds:
*Color.*—RHS 75D (Purple); flushed with RHS N77B (Darker purple), immature tube RHS 147D (Yellow-green), lower half (immature calyx) between RHS 144A (Yellow-green) and RHS 144B (Yellow-green), flushed RHS with N186C (Greyed-purple).
*Shape.*—Oblanceolate.
*Size.*—Length: 2.4 cm. Diameter: 0.5 cm.
*Rate of opening.*—Open approximately 4 days from stage described above.
Inflorescence:
*Blooming habit.*—Continuous once a year.
*Inflorescence type.*—Self-cleaning, compound terminal panicle.
*Natural flowering season.*—Summer to late summer (July to late-August).
*Height.*—15.6 cm.
*Width.*—15.1 cm.
*Fragrance.*—Moderate, sweet; typical *Phlox paniculata* scent.
*Flower number* (*per inflorescence*).—180.
*Quantity of flowers per lateral stem.*—20.
*Quantity of flower buds Per lateral stem.*—160.
*Quantity of flower and buds per plant.*—1500.
*Rate of flower opening.*—Approximately 25% of the flowers at any stage.
*Flower longevity on plant.*—10 days.
*Flower longevity as a cut flower.*—10 days.

Peduncle:
*Color.*—RHS 146A (Yellow-green).
*Length.*—Primary: 10.6 cm. Secondary: 5.2 cm.
*Diameter.*—Primary: 2.5 cm. Secondary: 0.15 cm.
*Angle.*—Primary peduncles average angle 0° (straight upright), secondary peduncles with an average angle of 45°.
*Strength.*—Strong.
Pedicel:
*Color.*—Between RHS 143A (Yellow-green) and RHS 144A (Yellow-green).
*Length.*—0.6 cm.
*Diameter.*—0.1 cm.
*Angle.*—Average angle 30° (0° to 60°) (0°=straight on top of the peduncle).
*Strength.*—Strong.
Florets:
*Type.*—Single.
*Shape.*—Salverform.
*Aspect.*—Upright to outward.
*Fragrance.*—Moderate, sweet; typical *Phlox paniculata* scent.
*Size.*—Height (flower depth): 2.7 cm. Diameter: 3.2 cm.
*Petals.*—Arrangement: Rotate. Shape: Spathulate, the lower 60% fused into a tube. Appearance: Dull, smooth. Number: 5, fused into a tube (lower 60% of each petal). Size: Length: 3.9 cm (lower 2.4 cm fused into a tube). Width: 1.8 cm. Apex: Rounded. Margin: Entire. Color (when opening): Upper surface: Between RHS 62B (Red-purple) and RHS 62D (Red-purple), base of free part RHS N74A (Red-purple), tube RHS N77D (Purple). Lower surface: Between RHS 69C (Red-purple) and RHS 69D (Red-purple), tube RHS 77D (Purple). Color (fully opened): Upper surface: Between RHS N155B (White) and pure white (Not on RHS chart), base of free part RHS N74A (Red-purple), tube RHS N77C (Purple). Lower surface: Pure white (Not on RHS Chart), tube RHS N77C (Red-purple). Color fading to: RHS N77A (Base of free part coloring more intense Red-purple). Texture (both surfaces): Smooth.
Calyx:
*Shape.*—Campanulate.
*Length.*—1.0 cm.
*Diameter.*—0.7 cm.
*Sepals.*—Arrangement: Rotate. Appearance: Smooth, dull. Number: 5. Shape: Linear. Apex: Narrow apiculate. Base: Lower 30% fused. Margin: Entire. Size: Length: 1.0 cm. Width: 0.2 cm. Color (mature): Upper surface: Between RHS 144A (Yellow-green) and RHS 144B (Yellow-green); heavily flushed with RHS N186C (Greyed-purple). Lower surface: Between RHS 144A (Yellow-green) and RHS 144B (Yellow-green); heavily flushed with RHS N186C (Greyed-purple). Color (immature): Upper surface: Between RHS 144A (Yellow-green) and RHS 144B (Yellow-green); flushed with RHS N186C (Greyed-purple). Lower surface: RHS 144B (Yellow-green); flushed with RHS N186C (Greyed-purple).
Reproductive organs:
*Stamens.*—Quantity: 5. Anther: Shape: Basifixed, oblong; filament implanted in petal. Length: 0.2 cm. Length of filament: 0.1 cm. Color: RHS 4D (Yellow).
*Pollen.*—Amount: Moderate. Color: RHS 4C (Yellow).

*Pistil.*—Quantity: 1. Length: 2.0 cm.

*Style.*—Length: 1.9 cm. Color: RHS 147B (Yellow-green) tinged with RHS 187A (Greyed-purple).

*Stigma.*—Shape: Cleft (3-parted). Color: Between RHS 150C (Yellow-green) and RHS 150D (Yellow-green).

*Ovary color.*—RHS 143A (Green).

Fruit and Seed Set:

*Seeds.*—Quantity: 3 seeds per fruit. Length: 0.3 cm. Diameter: 0.2 cm. Color: RHS 200A (Brown).

*Fruit.*—Quantity of fruit per lateral branch: 15. Quantity of fruit per plant: 135. Length: 1.2 cm. Diameter: 0.6 cm. Color: RHS 146A (Yellow-green). Texture: Smooth, glossy.

Disease and insect resistance: Good mildew resistance; no other particular resistance or susceptibility to diseases or insects noted to date.

COMPARISON WITH COMMERCIAL CULTIVARS

'Swizzle' differs from the commercial *Phlox paniculata* variety 'Graf Zeppelin' (unpatented), by having healthier foliage with thicker stems and a sturdier plant habit than 'Graf Zeppelin'. Additionally, 'Swizzle' has a more compact plant habit and flowers earlier in the season than 'Graf Zeppelin'.

While 'Swizzle' is similar to the commercial *Phlox* variety 'Grenadine Dream' (U.S. Plant patent application Ser. No. 11/725,797), in that both varieties have compact plant habits, similar plant heights, similar open-flower sizes, good mildew resistance and thick stems, 'Swizzle' differs from 'Grenadine Dream' by having pinkish-white overlapping petals around an intense, hot-pink eye while 'Grenadine Dream' has rich red-purple flowers. Additionally, 'Swizzle' has lighter colored foliage and a more pyramid-shaped flower head than 'Grenadine Dream'.

I claim:

1. A new and distinct cultivar of *phlox* plant as shown and described herein.

* * * * *